US012752121B2

(12) United States Patent
Palti et al.

(10) Patent No.: US 12,752,121 B2
(45) Date of Patent: Oct. 6, 2026

(54) MULTISITE LEADLESS CARDIAC RESYNCHRONIZATION

(71) Applicant: Cardoaid Ltd., Tirat Carmel (IL)

(72) Inventors: Yoram Palti, Haifa (IL); Rafael Beyar, Haifa (IL)

(73) Assignee: Cardoaid Ltd., Tirat Carmel (IL)

( * ) Notice: Subject to any disclaimer, the term of this patent is extended or adjusted under 35 U.S.C. 154(b) by 514 days.

(21) Appl. No.: 17/728,611

(22) Filed: Apr. 25, 2022

(65) Prior Publication Data

US 2022/0339451 A1 Oct. 27, 2022

Related U.S. Application Data

(60) Provisional application No. 63/180,336, filed on Apr. 27, 2021.

(51) Int. Cl.
*A61N 1/368* (2006.01)
*A61N 1/362* (2006.01)

(52) U.S. Cl.
CPC ....... *A61N 1/36843* (2017.08); *A61N 1/3627* (2013.01)

(58) Field of Classification Search
CPC .. A61N 1/36843; A61N 1/3627; A61N 1/362; A61N 1/3622

(Continued)

(56) References Cited

U.S. PATENT DOCUMENTS 6,868,289 B2 3/2005 Palti
2007/0055184 A1* 3/2007 Echt .................... A61N 1/3627 601/2

(Continued)

FOREIGN PATENT DOCUMENTS

EP 2769750 B1 1/2020
WO 2006045073 A1 4/2006

(Continued)

OTHER PUBLICATIONS

Bereuter, Gysin, Kueffer, Kucera, Niederhauser, Fuhrer, Heinisch, Zurbuchen, Obrist, Tanner, & Haeberlin, Leadless Dual-Chamber Pacing: A Novel Communication Method for Wireless Pacemaker Synchronization. JACC. Basic to translational science, 3(6), 813-823. (Year: 2018).*

(Continued)

*Primary Examiner* — Allen Porter
*Assistant Examiner* — Sefra D. Manos
(74) *Attorney, Agent, or Firm* — Potomac Law Group, PLLC

(57) ABSTRACT

Synchronized stimulation of cardiac tissue can be implemented by implanting two or more rectifier-based AM receivers into different positions within a subject's heart. Each receiver is tuned to a different frequency, and generates an output signal that is capable of stimulating cardiac tissue when a signal at the corresponding tuned frequency arrives at the receiver. An AM transmitter can activate any given one of the receivers by transmitting a signal into the subject's body at the proper frequency. A controller controls the transmitter by commanding the transmitter to transmit pulses of AC at different frequencies at different times, so that when those pulses are received by the correspondingly-tuned receivers, each of the receivers will generate respective output signals that stimulate respective parts of the heart at respective times to promote improved cardiac performance.

20 Claims, 9 Drawing Sheets

(58) Field of Classification Search
USPC .............................................................. 607/9
See application file for complete search history.

(56) References Cited

U.S. PATENT DOCUMENTS

| | | | | |
|---|---|---|---|---|
| 2012/0059433 | A1* | 3/2012 | Cowan | A61N 1/36007 607/51 |
| 2018/0071539 | A1* | 3/2018 | Hastings | A61N 1/37512 |
| 2019/0001139 | A1* | 1/2019 | Mishra | A61N 1/0556 |
| 2020/0238093 | A1 | 7/2020 | Kim et al. | |
| 2022/0008736 | A1* | 1/2022 | Babakhani | A61N 1/37288 |

FOREIGN PATENT DOCUMENTS

| | | | |
|---|---|---|---|
| WO | 2013111137 | A2 | 8/2013 |
| WO | 2020106862 | A1 | 5/2020 |

OTHER PUBLICATIONS

International Search Report and Written Opinion issued in application PCT/IB2022/053831 dated Jul. 21, 2022.

* cited by examiner

MULTISITE LEADLESS CARDIAC RESYNCHRONIZATION

CROSS REFERENCE TO RELATED APPLICATIONS

This application claims the benefit of U.S. Provisional Application 63/180,336, filed Apr. 27, 2021, which is incorporated herein by reference in its entirety.

FIELD OF THE INVENTION

The present invention relates, generally, to apparatuses and methods for multisite stimulation of tissues in a living body, in particular heart tissue in a living body, using leadless stimulation to promote normal cardiac activity.

BACKGROUND

Heart failure is one of the major causes of morbidity and mortality in the western world. About 6.2 million adults in the United States have heart failure, and in 2018, over 13% of all US deaths were attributable to heart failure.

In many cases, asynchrony of the heart contractions contributes to ventricular dysfunction and to heart failure. When certain segments of the heart, for example, at positions within the left ventricle (LV), contract with incorrect timing with respect to other positions within the heart tissue, they fail to contribute positively to stroke volume and cardiac output. Cardiac resynchronization therapy (CRT) introduced the concept of multisite pacing to synchronize the delayed segments of the ventricle. CRT improves heart function by improving electrical (and consequently mechanical) coordination and thus pump efficiency. CRT is traditionally accomplished by pacing of the right ventricle (RV) using an endocardial lead, and pacing the LV using an epicardial lead in the coronary sinus. Such pacing is provided to restore interventricular and intraventricular synchrony. This procedure improves LV contractility, stroke volume, and ejection fraction. However, CRT is not uniformly effective, and careful patient selection, lead positioning, and device programming are necessary to maximize its benefits.

As a procedure to increase the efficiency of CRT, it has been proposed that pacing from more than one LV site, such as is done today through the coronary sinus lead, may improve resynchronization and outcomes. It has been shown in small, randomized trials that the use of two epicardial coronary venous leads, as compared with the use of only one such lead, improves acute hemodynamic response, EF, LV end-systolic volume, and symptoms of heart failure.

Pacing leads that go through the vasculature are the standard today. Although such leads are reliable and effective, complications are common because the lead is subject to repetitive mechanical motion with each cardiac cycle, exposing its constituent materials to mechanical stress and fracture. This type of lead presents other hazards, as it can serve as a conduit for bacterial entry to the blood pool. Moreover, leads are inherently thrombogenic, eliciting fibrotic reactions that make removal technically challenging. Lead thrombogenicity also introduces a risk of stroke in the setting of venous systemic shunts. Lastly, when crossing the tricuspid valve, a lead can impinge on leaflet motion and cause significant tricuspid regurgitation, impairing the response to cardiac resynchronization and worsening heart failure.

Leadless endocardial LV pacing holds promise in that it may be more physiological, afford greater opportunities for LV pacing site selection, lead to a greater CRT response with lower risk of arrhythmia, eliminate phrenic nerve stimulation, and mitigate against the risks of mitral regurgitation and lead-related thrombus. However, the technology is early in its development, and there are many unknowns.

SUMMARY OF THE INVENTION

One aspect of the invention is directed to a first apparatus for stimulating a heart in a living body. The first apparatus comprises an AM transmitter having a controllable output frequency. The AM transmitter is configured to generate a first-frequency output signal in response to a first control signal and to generate a second-frequency output signal in response to a second control signal. The first frequency is at least 50 kHz, the second frequency is at least 50 kHz, and the first frequency is different from the second frequency. The first apparatus also comprises a first AM receiver configured for implantation at a first position within the heart. The first AM receiver includes a first antenna, at least one first rectifier, and a first filter that is tuned to the first frequency. The first AM receiver is configured to (a) generate a first demodulated output signal that is capable of stimulating cardiac tissue when the first-frequency output signal arrives at the first antenna and (b) not to generate an output signal that is capable of stimulating cardiac tissue when the second-frequency output signal arrives at the first antenna. The first apparatus also comprises a second AM receiver configured for implantation at a second position within the heart. The second AM receiver includes a second antenna, at least one second rectifier, and a second filter that is tuned to the second frequency. The second AM receiver is configured to (a) generate a second demodulated output signal that is capable of stimulating cardiac tissue when the second-frequency output signal arrives at the second antenna and (b) not to generate an output signal that is capable of stimulating the cardiac tissue when the first-frequency output signal arrives at the second antenna. The first apparatus also comprises a controller configured to generate the first control signal and the second control signal and to control timing and duration of the generated first and second control signals so that the generated first and second control signals cause the AM transmitter to generate the first-frequency output signal and the second-frequency output signal at appropriate times during a cardiac cycle so that when the first-frequency output signal and the second-frequency output signal are received by the first AM receiver and the second AM receiver, respectively, the first AM receiver and the second AM receiver will generate the respective first and second demodulated output signals that stimulate respective parts of the heart to promote improved cardiac performance.

In some embodiments of the first apparatus, the controller is configured to control the timing of the generated first and second control signals such that there is a first delay between initiation of the first control signal and initiation of the second control signal. The first delay is one of a predetermined delay, a selected delay based on a medical characteristic of the body, and a delay determined in accordance with a response of the cardiac tissue to at least one of the first and second demodulated output signals.

In some embodiments of the first apparatus, the AM transmitter is configured to be connectable to the body external to the heart. In some embodiments of the first apparatus, each of the at least one first rectifier and the at least one second rectifier comprises four diodes arranged in a full-wave rectifier circuit. In some embodiments of the first apparatus, each of the at least one first rectifier and the at least one second rectifier comprises a diode arranged in a half-wave rectifier circuit. In some embodiments of the first apparatus, the first frequency is between 100 kHz and 1 MHz and the second frequency is between 100 kHz and 1 MHz.

Some embodiments of the first apparatus further comprise a third AM receiver configured for implantation at a third position within the heart. The third AM receiver includes a third antenna, at least one third rectifier, and a third filter. The AM transmitter is further configured to generate a third-frequency output signal in response to a third control signal. The third frequency is at least 50 kHz, and the third frequency is different from the first frequency and also different from the second frequency. The third filter is tuned to the third frequency. The third AM receiver is configured to (a) generate a third demodulated output signal that is capable of stimulating cardiac tissue when the third-frequency output signal arrives at the third antenna and (b) not to generate an output signal that is capable of stimulating cardiac tissue when the first-frequency output signal arrives at the third antenna or when the second-frequency output signal arrives at the third antenna. The controller is further configured to generate the third control signal and to control timing and duration of the generated first, second, and third control signals so that the generated first, second, and third control signals cause the AM transmitter to generate the first-frequency output signal, the second-frequency output signal, and the third-frequency output signal at appropriate times during a cardiac cycle so that when the first-frequency output signal, the second-frequency output signal, and the third-frequency output signal are received by the first, second, and third AM receivers, respectively, the first, second, and third AM receivers will generate the respective first second, and third demodulated output signals that stimulate respective parts of the heart to promote improved cardiac performance. The first AM receiver is configured not to generate an output signal that is capable of stimulating cardiac tissue when the third-frequency output signal arrives at the first antenna, and the second AM receiver is configured not to generate an output signal that is capable of stimulating cardiac tissue when the third-frequency output signal arrives at the second antenna. Optionally, in these embodiments, the controller is configured to control the timing of the generated first, second, and third control signals such that there is a second delay between initiation of the second control signal and initiation of the third control signal, wherein each of the first and second delays is one of a predetermined delay, a selected delay based on a medical characteristic of the body, and a delay determined in accordance with a response of the cardiac tissue to at least one of the first, second, and third demodulated output signals. Optionally, the third frequency is between 100 kHz and 1 MHz.

Another aspect of the invention is directed to a first method for stimulating a heart in a living body. The first method comprises transmitting an AM signal at a first frequency at certain first times and an AM signal at a second frequency at certain second times. The first frequency is at least 50 kHz, the second frequency is at least 50 kHz, and the first frequency is different from the second frequency. The first method also comprises receiving the AM signal at the first frequency at a first position within the heart and, responsive to receipt at the first frequency, generating a corresponding first demodulated output signal that is capable of stimulating cardiac tissue. An output signal that is capable of stimulating cardiac tissue is not generated when the AM signal at the second frequency arrives at the first position. The first method also comprises receiving the AM signal at the second frequency at a second position within the heart and, responsive to receipt at the second frequency, generating a corresponding second demodulated output signal that is capable of stimulating cardiac tissue. An output signal that is capable of stimulating cardiac tissue is not generated when the AM signal at the first frequency arrives at the second position. And the first method also comprises controlling generation, timing, and duration of the AM signal at the first frequency and the AM signal at the second frequency at appropriate times during a cardiac cycle so that when the AM signal at the first frequency and the AM signal at the second frequency are received at the first and second positions, respectively, the generated first and second demodulated output signals will stimulate respective parts of the heart to promote improved cardiac performance.

Some instances of the first method further comprise the step of controlling the timing of the AM signal at the first frequency and the AM signal at the second frequency such that there is a first delay between initiation of the first AM signal at the first frequency and initiation of the second AM signal at the second frequency. The first delay is one of a predetermined delay, a selected delay based on a medical characteristic of the body, and a delay determined in accordance with a response of the cardiac tissue to at least one of the first and second demodulated output signals.

In some instances of the first method, the transmitting of the AM signal occurs through the body from a position of the body external to the heart. In some instances of the first method, the first frequency is between 100 kHz and 1 MHz and the second frequency is between 100 kHz and 1 MHz.

Some instances of the first method further comprise transmitting the AM signal at a third frequency at certain third times. The third frequency is at least 50 kHz, and the third frequency is different from the first frequency and also different from the second frequency. These instances also comprise receiving the AM signal at the third frequency at a third position within the heart and, responsive to receipt at the third frequency, generating a third demodulated output signal that is capable of stimulating cardiac tissue. An output signal that is capable of stimulating cardiac tissue is not generated when either the AM signal at the first frequency or the AM signal at the second frequency arrives at the third position. In these instances, the controlling step includes the steps of controlling generation of the AM signal at the third frequency and controlling timing and duration of the AM signals at the first, second, and third frequencies at appropriate times during a cardiac cycle so that when the AM signals at the first, second, and third frequencies are received at the first, second, and third positions, respectively, the generated first second, and third demodulated output signals will stimulate respective parts of the heart to promote improved cardiac performance. No output signal capable of stimulating cardiac tissue is generated when the AM signal at the third frequency is received at either the first position or the second position. Optionally, in these instances, the controlling step controls the timing of the AM signals at the first, second, and third frequencies such that there is a second delay between initiation of the AM signal at the second frequency and initiation of the AM signal at the third frequency. Each of the first and second delays is one of a predetermined delay, a selected delay based on a medical characteristic of the body, and a delay determined in accordance with a response of the cardiac tissue to at least one of the first, second, and third demodulated output signals. Optionally, in these instances, the third frequency is between 100 kHz and 1 MHz.

Another aspect of the invention is directed to a second apparatus for stimulating designated animal tissue in a living body. The second apparatus comprises an AM transmitter having a controllable output frequency. The AM transmitter is configured to generate a first-frequency output signal in response to a first control signal and a second-frequency output signal in response to a second control signal. The first frequency is at least 50 kHz, the second frequency is at least 50 kHz, and the first frequency is different from the second frequency. The second apparatus also comprises a first AM receiver configured for implantation at a first position within the tissue. The first AM receiver includes a first antenna, at least one first rectifier, and a first filter that is tuned to the first frequency. The first AM receiver is configured to (a) generate a first demodulated output signal that is capable of stimulating the tissue when the first-frequency output signal arrives at the first antenna and (b) not to generate an output signal that is capable of stimulating the tissue when the second-frequency output signal arrives at the first antenna. The second apparatus also comprises a second AM receiver configured for implantation at a second position within the tissue. The second AM receiver includes a second antenna, at least one second rectifier, and a second filter that is tuned to the second frequency. The second AM receiver is configured to (a) generate a second demodulated output signal that is capable of stimulating the tissue when the second-frequency output signal arrives at the second antenna and (b) not to generate an output signal that is capable of stimulating the tissue when the first-frequency output signal arrives at the second antenna. The second apparatus also comprises a controller configured to generate the first control signal and the second control signal and to control timing and duration of the generated first and second control signals so that the generated first and second control signals cause the AM transmitter to generate the first-frequency output signal and the second-frequency output signal at appropriate times during an activity of the tissue so that when the first-frequency output signal and the second-frequency output signal are received by the first AM receiver and the second AM receiver, respectively, the first AM receiver and the second AM receiver will generate the respective first and second demodulated output signals that stimulate the tissue.

In some embodiments of the second apparatus, the controller is configured to control the timing of the generated first and second control signals such that there is a first delay between initiation of the first control signal and initiation of the second control signal. The first delay is one of a predetermined delay, a selected delay based on a medical characteristic of the tissue, and a delay determined in accordance with a response of the tissue to at least one of the first and second demodulated output signals.

In some embodiments of the second apparatus, the AM transmitter is configured to be connectable to the body external to the tissue. In some embodiments of the second apparatus, the first frequency is between 100 kHz and 1 MHz and the second frequency is between 100 kHz and 1 MHz.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

The embodiments described herein rely on applying alternating electric fields of at least 50 kHz to the living body by means of external electrodes, i.e., external to the target tissue to be stimulated, together with implantation of rectifier-based receivers at the targets for stimulation. The high frequency alternating sinusoidal electric fields themselves do not have stimulating power, as the tissue cells and their membranes have relatively low frequency electric responses and, therefore, they integrate the alternating potential such that the effective potential differences are reduced to zero. However, when a rectifier-based receiver (e.g., a receiver based on a single diode) is implanted in the tissue, then the AC is “half rectified” at the two points of contact of the rectifier. Thus, when high frequency alternating potential pulses are applied to the body volume by remote electrodes positioned on, e.g., the surface, subcutaneous tissues, etc. of the living body, the rectified, i.e., unidirectional, electric pulses can affect the cells and tissues located in the electric field. When the AC pulse duration is in the range of 0.1-10 msec, and the potential differences are of 0.1-100 volts, excitable cells are stimulated.

When rectifier-based receivers are implanted at the various body positions where one wants to have stimulation and activation, and high frequency AC pulses are applied to the implanted rectifier-based receivers remotely, for example, from the body surface, the tissues in the vicinity of the negative poles of the rectifiers are stimulated. Such tissues can be, for example, peripheral nerves, neurons, skeletal muscles, cardiac muscles, and smooth muscles (of blood vessels, sphincters, etc.). Correspondingly, the positive poles of the rectifiers can cause inhibition. Differentiation between stimulation and inhibition can be achieved by having different electrode contact areas and/or polarity. This is because the larger the contact area, the smaller the current density and consequently the smaller the stimulation/inhibition efficacy.

Although embodiments of the invention can be used in many types of tissues in vivo, the description below focusses on multisite stimulation of the heart and/or inhibition of cardiac tissue as the prime example, and on positions within the brain as a secondary example. But notably, other positions within the body can also be stimulated/inhibited to promote optimal performance of the target tissue.

In a first preferred embodiment, an apparatus, labeled herein the "Multisite Leadless Cardiac Stimulator (MLCS)," will be discussed below in the following sections: Alternating Sine-wave Pulse Potential Generator, ASPPG 1; Field Generating Electrodes (FGE) 2; The Implanted Rectifier-based receivers 3; Multiple Implanted Rectifier-based receivers 3; Auxiliary Circuits 40 of the Rectifier-based receivers 3; and Controller 7.

1. The AC Pulse Generator ASPPG

Figure 1A:
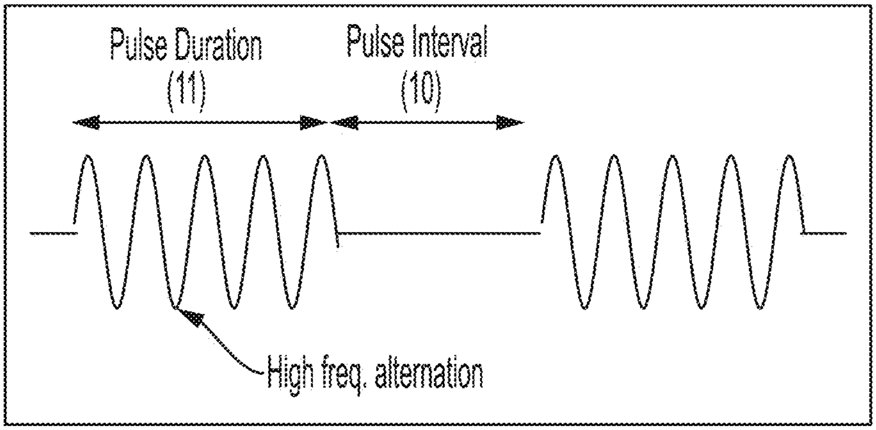
FIG. 1A is an illustration of pulse durations/pulse intervals used in preferred embodiments of the present invention.
Figure 8:
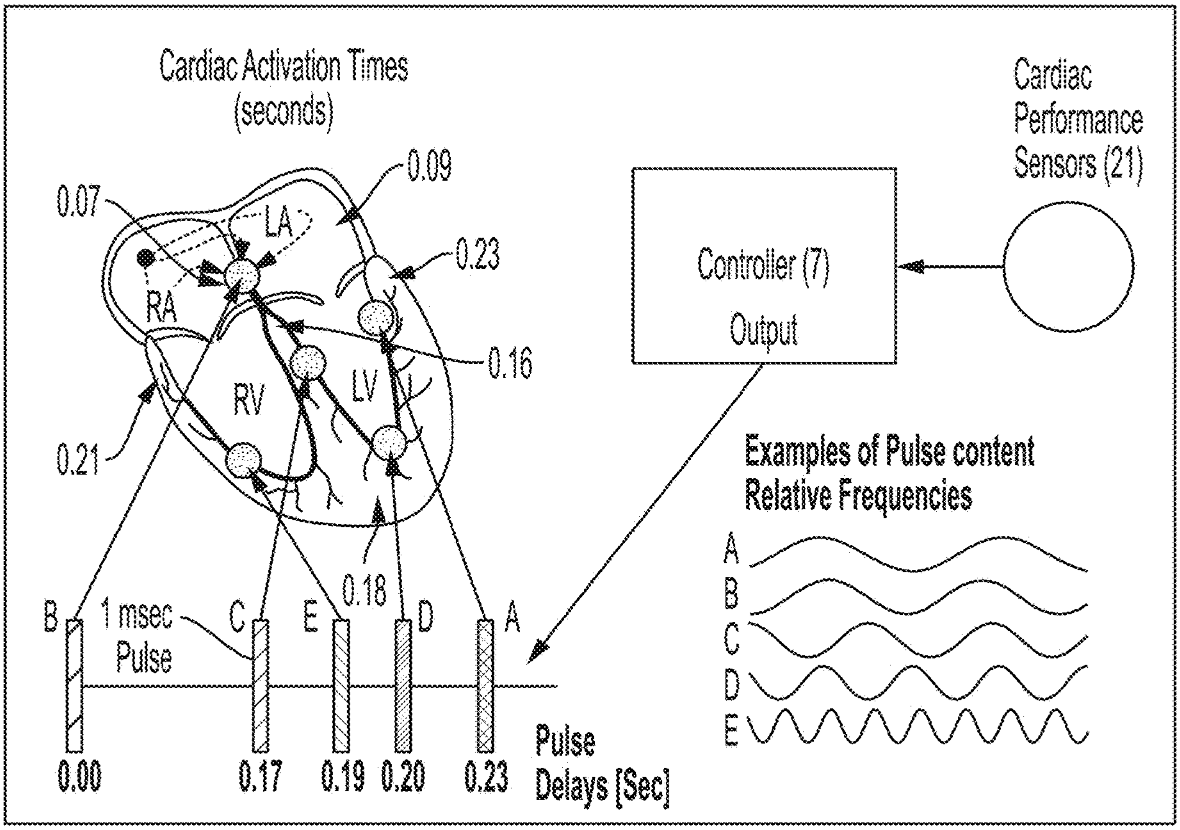
FIG. 8 is an illustration of cardiac activation times in accordance with a preferred embodiment of the present invention.
Figure 9:
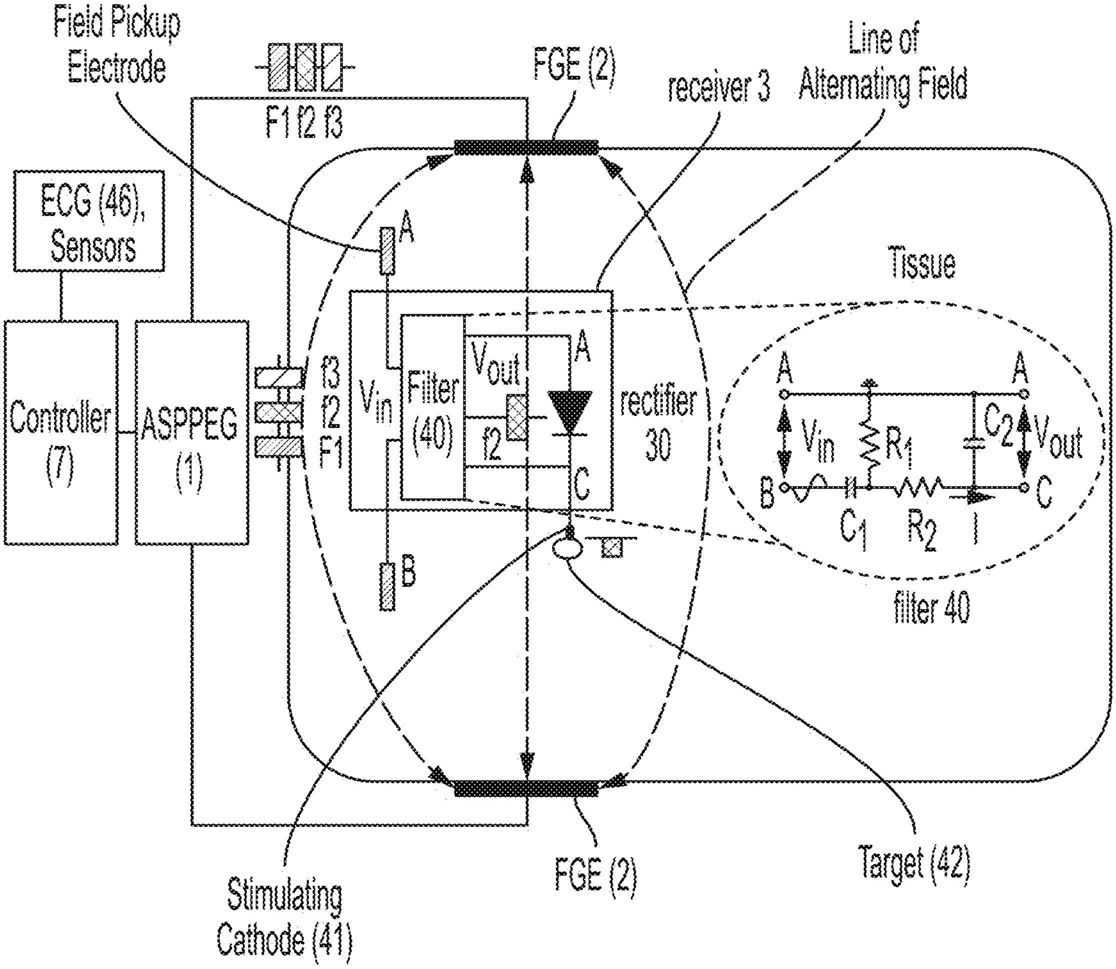
FIG. 9 is an illustration of another embodiment of the present invention.
Figure 11:
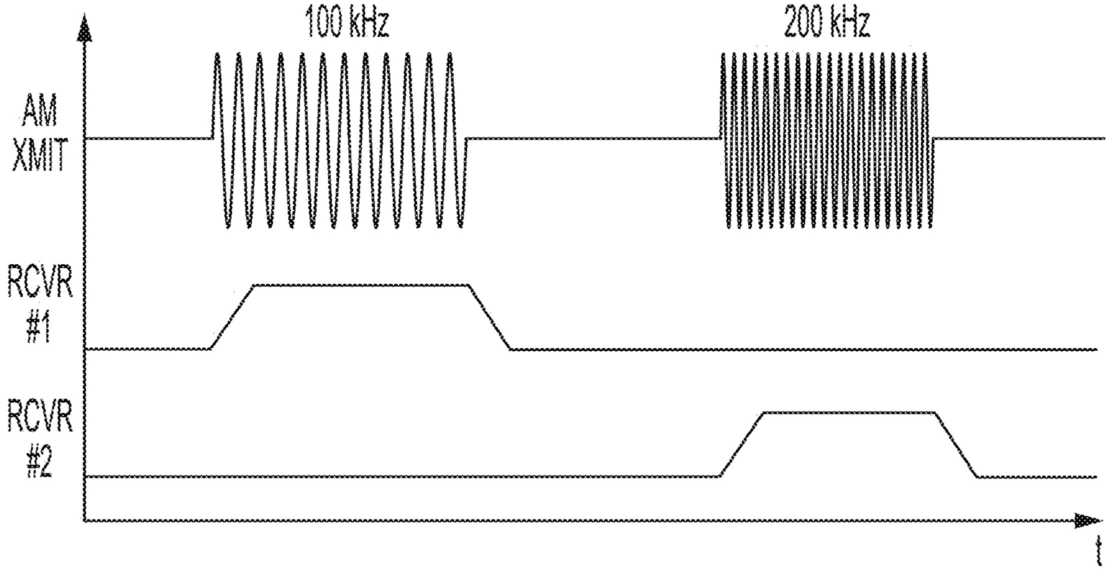
FIG. 11 is a timing diagram illustrating the respective activation times of plural rectifier-based receivers in the FIG. 10 embodiment.

The ASPPG 1 (FIG. 2) is a type of AM transmitter, specifically a line or battery powered sine wave oscillator that outputs alternating sine-wave potential pulses. As shown in FIG. 1A, the pulse duration 11 of the pulses generated by the ASPPG 1 is typically in the range of 0.1-10 msec, and their potential difference amplitudes are typically of 0.1-100 volts. The pulse intervals 10 are typically 0.02-5 sec. The output of the ASPPG 1 is delivered via a pair, or more, of field generating electrodes (FGE) 2, making contact with the patient's skin, subcutaneous tissue, cardiac tissue, or other tissues. The pulse parameters are set by means of a controller 7 (FIGS. 8, 9, 11). These parameters can be preset, or adjusted according to cardiac performance or patient needs, etc. The controller 7 will be discussed in detail below.

Figure 1B:
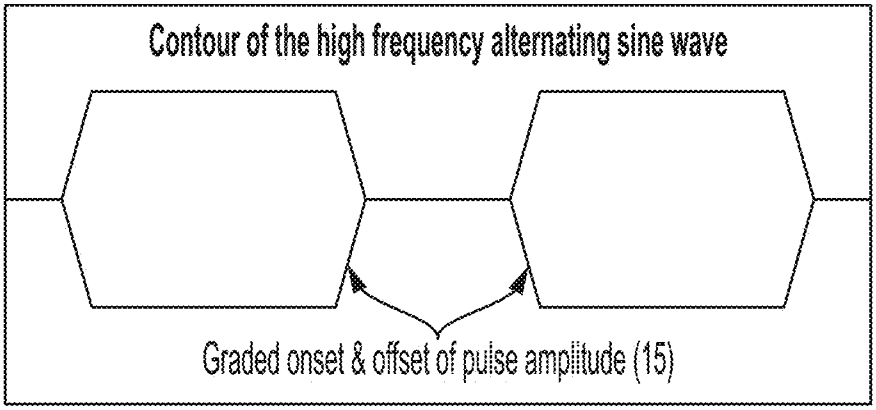
FIG. 1B is an illustration of a sine wave contour used in preferred embodiments of the present invention.

In order to avoid unwanted stimulation of excitable tissue, the frequency of the AC pulses generated by the ASPPG 1 should be above 50 kHz. The specific frequency used is not critical, as AC pulses at a frequency above 50 kHz do not affect the rectified pulse efficacy. However, other considerations may be involved. These considerations include, for example, voltage losses on the electrode insulation, if used, due to the frequency dependence of the electric impedance, changes in field distribution with frequency, etc. In some embodiments, the frequency is 0.1-1.0 MHz, and in some embodiments the frequency is 100-300 kHz. But other embodiments can operate outside these ranges. Additionally, to avoid a potential stimulating effect of the pulse onset or offset, a gradual increase and decrease 15 of the amplitude of the alternating sine-wave (e.g., ramping the amplitude up at the beginning of each pulse of AC and ramping the amplitude down at the end of each pulse of AC) may be employed, as shown in FIG. 1B.

Figure 2:
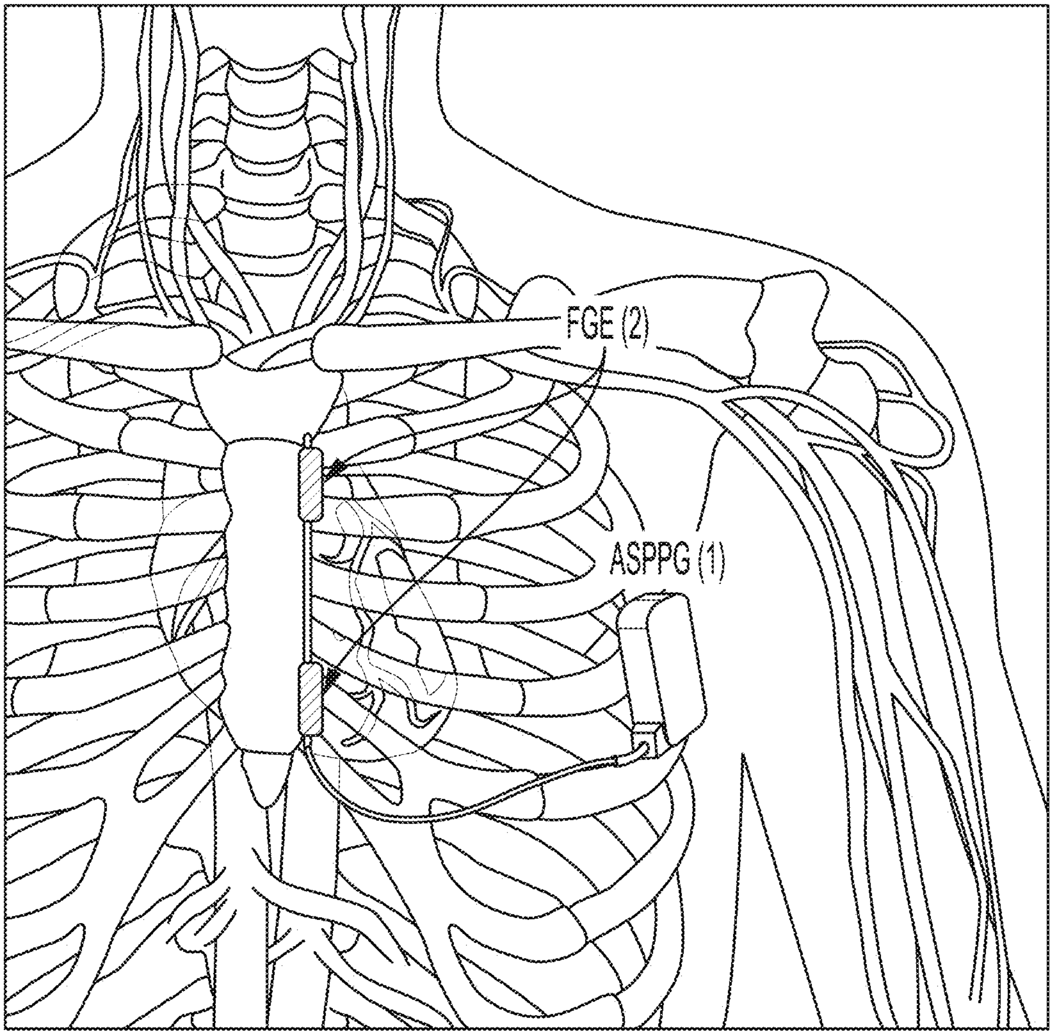
FIG. 2 is an illustration of an AM transmitter and electrodes used in preferred embodiments of the present invention as positioned on a human body.

As shown in FIG. 2, the ASPPG 1 can be connectable to the body external to the target heart tissue. For example, the ASPPG 1 can be worn by the patient external to the target heart tissue, for example, positioned on the body surface or, in a proper casing, implanted in the body, for example subcutaneously in the chest wall, in a manner similar to the common pacemaker placement. Alternatively, when miniaturized, the ASPPG 1 can be implanted within the heart, but still remote from the target heart tissue, e.g., the left ventricle.

2. The Field Generating Electrodes (FGE)

As shown in FIG. 2, in this embodiment two field generating electrodes (FGE) 2 are energized by ASPPG 1 to which they are connected by appropriate leads. The electrodes 2 are designed to, when driven by the ASPPG 1, generate an effective alternating electric field in the target areas. The FGEs 2 are positioned on or in the subject's body so as to generate in the patient's body an electric field that satisfies the conditions listed below. Additional electrodes and alternate electrode arrangements may be added, depending on individual circumstances.

Each part of electrodes 2 that makes contact with the tissues is preferably made of a biocompatible material (e.g., metal, graphene, or another electric conductor). It can have a mechanical support backing and preferably is insulated by a dielectric having a sufficiently high dielectric constant that, for its given thickness and sine-wave frequency of pulse, will have an electric impedance that is low relative to the impedance of the tissues positioned between the electrodes. Such electrodes and the rationale behind them are described, for example, in U.S. Pat. No. 6,868,289 to Palti, which is incorporated herein by reference in its entirety.

It should be noted that the FGE electrode 2 cannot pass DC and low frequency potentials/currents, such as the those of the power line. The electrode insulation prevents the flowing currents from affecting the cellular ion contents, etc.

The distribution of the alternating electric field generated by the FGE electrodes 2 in the chest depends on the geometry and electrical properties of the different affected components (tissues), and depends mainly on their relative electric conductance. Typically, the amplitude of cardiac pacing pulses is in the range of 1 volt, with pulse duration of 0.5 msec (current amplitude 10 μA), and the field generated potential difference between the two rectifier electrodes (discussed below) making contact with the tissue should be in the range of 1-2 volts. Assuming that the length of the rectifier, and thus the distance between its two electrodes, is 1-3 cm, the AC fields generated by the FGE electrodes 2 should be in the range of 1-2 V/cm.

Figure 3:
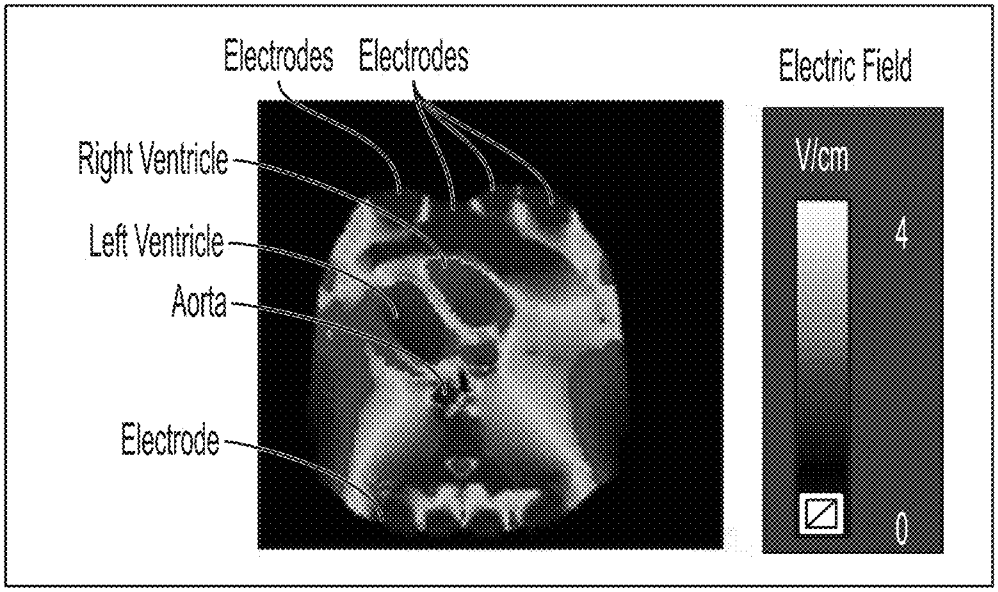
FIG. 3 is an illustration of a simulated electric field distribution in a human torso.

Simulation of a 200 kHz electric field distribution in a human torso, as generated by four FGE electrodes 2 positioned on the chest front and back, is depicted in FIG. 3. Notably, the field intensity in the ventricle walls is 1-3 V/cm in many portions of the heart which, as explained above, is sufficient to generate effective cardiac pacing pulses.

3. The Implanted Rectifier-Based Receivers

The alternating sine-wave potential pulses generated by the FGE electrodes 2 cannot stimulate excitable tissues because the tissue cells and their membranes have relatively slow electric responses. Therefore, the cells/membranes integrate the alternating potential such that the effective potential differences are reduced to zero. In contrast, when rectifier electrodes make contact with two points in the tissue, the alternating electric field at the two contact points is rectified. Under these conditions the rectified, i.e., unidirectional, electric pulses can potentially stimulate the excitable cells in the electric field. When the AC pulse duration 11 is in the range of 0.1-10 msec, and the potential differences between the electrodes are 0.1-1 Volts, stimulation of excitable cells can occur. Numerous miniature rectifier-based receivers 3 can be implanted in the heart muscle, e.g., as depicted in FIG. 4.

The implantation of multiple rectifier-based receivers 3 can be done by means of a number of procedures, for example, by means of a catheter inserted through the venous system to the right atrium and other cardiac chambers, as is currently done in many clinical procedures. The implantation can be in the endocardium of the LV wall or, for example, through the coronary sinus to the epicardium. An alternative mode of insertion is by insertion through the chest wall using a hypodermic needle. Because the implant is miniaturized, the needle diameter can be small. The required rectifier-based receivers 3 are passive elements the size of which can be well under a millimeter, even together with the described auxiliary circuits 40. Thus, multiple insertions at multiple sites can be easily achieved.

Figure 4A:
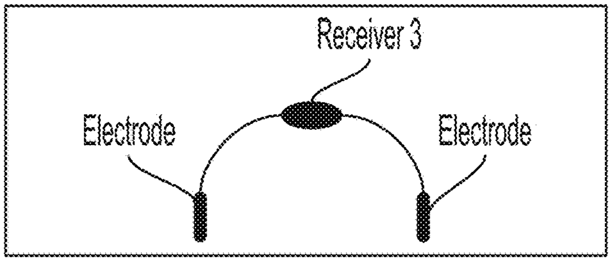
FIGS. 4A-4C are illustrations of receivers suitable for use in the preferred embodiments.
Figure 4B:
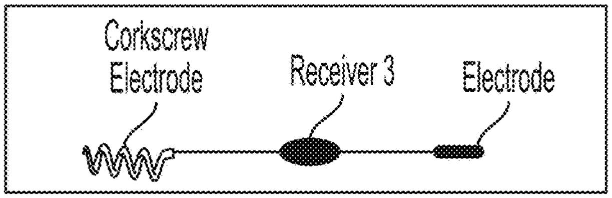
Figure 4C:
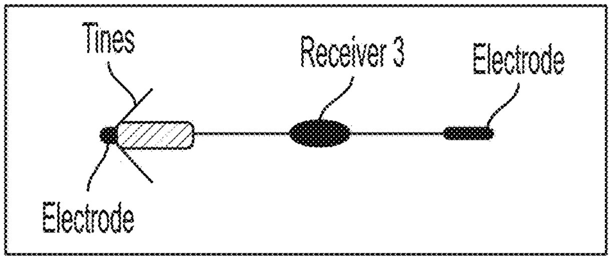

The implanted rectifier-based receivers 3, which are to be insulated by bio and hemo compatible materials, must have at least two electric contact points—electrodes. FIGS. 4A-4C depict three alternative approaches. In each of these figures, one of the contact points is preferably inserted and anchored in the cardiac muscle, while the other can make contact with another point of the muscle (as depicted in FIG. 4A) or make contact with the blood (as depicted in FIG. 4B). Anchoring can be made as is currently practiced, for example by a metal corkscrew (as depicted in FIG. 4B) that also serves as a muscle contact point. Conventional tines can also be used (as depicted in FIG. 4C). The electrode electric contact point materials can be, for example, stainless steel, platinum, gold, graphene, etc. Leads connecting the rectifier with the electrodes can be made of Nitinol with a selected shape memory such that, after insertion, it bends to a shape similar to the one depicted in FIG. 4A.

As the stimulation is a relatively high alternating current, the electrodes can be coated with a thin, high dielectric constant insulator, as described for the FGE electrodes 2.

Note that each rectifier-based receiver 3 includes an antenna to receive the incoming AC signal. In some embodiments, this antenna may be a discrete component that is connected to one terminal of the rectifier (e.g., the diode). In other embodiments where the rectifier (e.g., the diode) is supplied with leads that are sufficiently long, a lead of the rectifier can serve as the antenna that receives the incoming AC signal.

Each rectifier-based receiver 3 preferably includes at least one rectifier arranged in an electrical circuit (e.g., as described below in connection with 7C), combined with a frequency-selective filter (e.g., as described below in connection with FIG. 7D).

3a. Multiple Implanted Rectifier-Based Receivers

As is well known and documented, the stimulus that elicits the excitation of the myocytes normally originates at the SA (sinoatrial) node, spreads in the atria in non-specific pathways, reaches the AV (atrioventricular) node and from there it propagates along the branches of the atrioventricular bundle (bundle of His) along the septum, to the apex and then up to the base of the heart. The normal spread of excitation and contraction induces a very effective blood ejection from the ventricles to the pulmonary arteries and aorta. Pacemakers designed for re-synchronization (Cardiac Resynchronization Therapy—CRT) usually employ three cardiac stimulating points, activated at selected delays, in an attempt to improve cardiac output (CO) in CHF patients. Such patients are called periodically for "resynchronization therapy" to adjust the pulse delays so as to optimize CO, as determined usually by echo-cardiography.

Figure 5A:
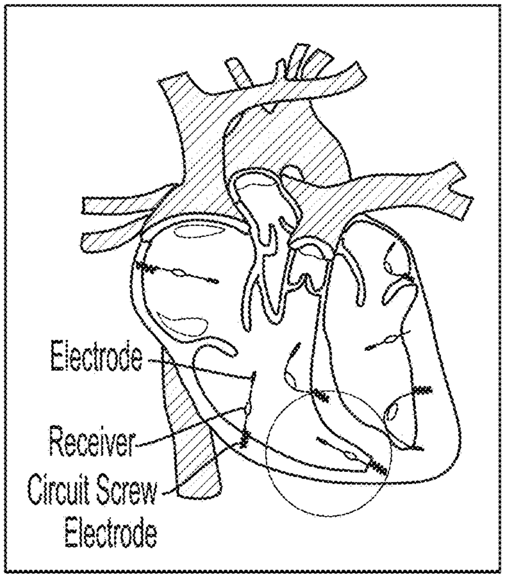
FIG. 5A is an illustration of an example of plural cardiac points (positions) that may be stimulated in accordance with preferred embodiments of the invention.
Figure 5B:
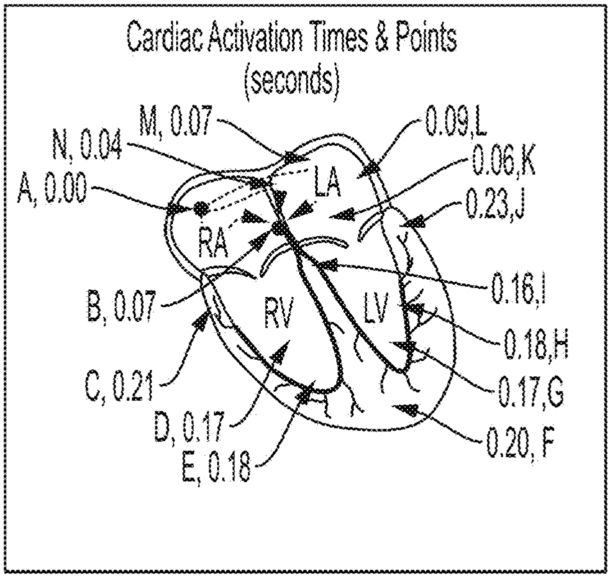
FIG. 5B is an illustration of the corresponding cardiac times of stimulation in this example.

FIG. 5A depicts an example of implanted rectifier-based receivers 3 at respective cardiac locations, and FIG. 5B depicts an example of the corresponding measured delays in the normal activation at the various cardiac locations. The 14 illustrated points (ends of arrows, A through L) or any fraction of them, can be used for stimulation by implanting at least two rectifier-based receivers 3 that are activated at respective relative time delays (relative to the time of activation (natural or induced)) of the SA node pacemaker. In some subjects, a relatively small number of stimulation points (e.g., 2 or 3) that are activated at respective times in each cardiac cycle may be sufficient to provide improved cardiac function. But in other subjects, a larger number of stimulation points may be necessary to sufficiently re-synchronize the operation of the heart.

Figure 7A:
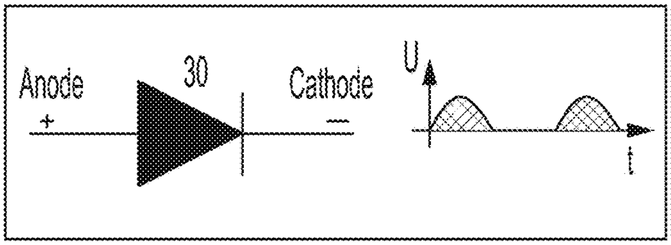
FIG. 7A is a circuit diagram of a half-wave rectifier circuit and its resultant rectified signal.
Figure 7C:
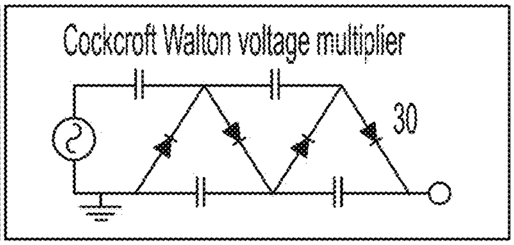
FIG. 7C is a circuit diagram of a voltage multiplier that provides rectification and voltage amplification.
Figure 7B:
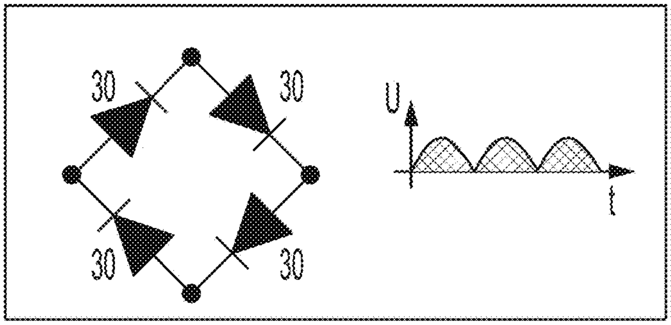
FIG. 7B is a circuit diagram of a full-wave rectifier circuit and its resultant rectified signal.
Figure 7D:
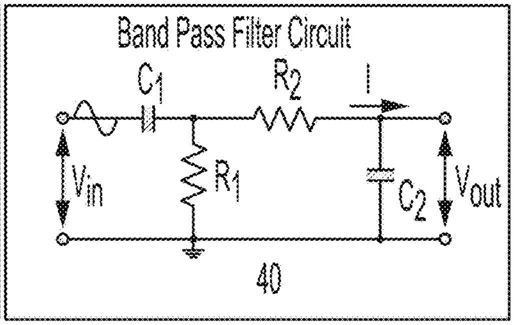
FIG. 7D is a diagram of a band pass filter circuit.

The activation delays are achieved and controlled as follows:

Each implanted rectifier-based receiver 3 includes at least one rectifier 30 and a frequency-selective filter 40 (e.g., a bandpass filter), such as the one depicted in FIG. 7D. The bandpass of each of the filters 40 is different. The controller 7 that controls the output of the alternating sine-wave pulse potential generator ASPPG 1, activates the ASPPG 1 such that it outputs to the Field Generating Electrodes (FGE) 2 pulses each consisting of an alternating wave of a different frequency and given at a selected delay. A compound waveform, including plural frequencies matching plural filter bandwidths of respective rectifier-based receivers 3, can also be used. Optionally, a resonating circuit tuned to the specific activating frequency can be added to the stimulating electrode to locally increase the stimulating current or voltage.

These delays can be preprogramed or selected for each patient on the basis of available information or by using the known resynchronization procedures.

Because some processes in the failing heart, including the contraction velocity (FIG. 6), are slower than normal, the delays can be corrected accordingly (e.g., to advance the time of the contraction).

The rectifiers 30 (e.g., diodes) used in the rectifier-based receivers 3 should advantageously have a forward resistance of a few ohms, i.e., low relative to the impedance of the tissue between the contact points.

The choice of the optimal delays can also be made on the basis of on-line measurements of cardiac performance sensors. In this case the delays may be changed by an appropriate algorithm that selects the optimal set of delays that provide a set of criteria for optimal performance.

3b. Auxiliary Circuits of the Rectifier-Based Receivers

The tissue stimulation can be achieved by a number of types of rectifiers 30 (e.g., diodes), that can be associated with selected passive or active circuits. For example, in some embodiments, the simplest version of a rectifier-based receiver 3 uses a single rectifier 30 with two lead wires inducing "half wave rectification" (FIG. 7A). In other embodiments, the rectifier-based receiver 3 may comprise a diode bridge that includes four rectifiers 30 and provides full rectification (FIG. 7B) that provides more stimulating current. Another embodiment is a voltage multiplier circuit like the one depicted in FIG. 7C that provides both rectification and voltage amplification.

Important types of circuits that can be associated with the rectifier-based receivers are various types of band pass filters 40, such as the one depicted, as an example, in the schematic of FIG. 7D. The use of bandpass filters 40 or similar elements can make it possible to separately activate multiple stimulating rectifier-based receivers, including activations at selected delays. This type of activation can allow optimization of the cardiac pumping function by activating the different sections of the cardiac muscle at the ventricles and at the atria in an optimal sequence.

4. The Controller

The main task of controller 7 is to optimize the cardiac muscle contraction and the generated cardiac performance and specifically cardiac output (CO) and, when relevant, the coronary perfusion. The efficient cardiac pumping action is achieved by stimulation of the cardiac muscles at selected locations at timings that produce the most effective pumping action. FIG. 8 illustrates an example of such locations and the times the normally conducted stimulus reaches them. The timing is given as delays relative to the initial stimulation time. The specific stimulation time of the different rectifier-based receivers 3 is achieved by means of the specific bandpass filter 40 within any given rectifier-based receiver 3. Controller 7 causes the output, at the selected delays, to the Field Generating electrodes 2, relatively short pulses (for example, 0.5 msec) consisting of different frequencies. The bandpass filter of each rectifier-based receiver 3 determines which of the pulses activates a specific rectifier-based receiver 3 at the intended delay.

Figure 6:
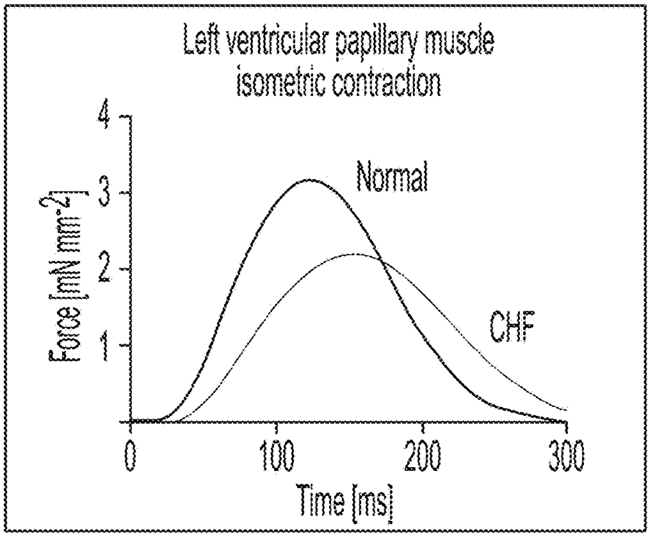
FIG. 6 is an illustration of left ventricular papillary muscle isometric contraction for a normal heart and a heart with congestive heart failure.

The cardiac performance optimization can be based on, for example, a predetermined stimulation protocol, manual adjustment of the stimulation times, or the determination of the optimal delays, at the different rectifier-based receiver locations, on the basis of the information received from the sensors of cardiac function (21). Such a sensor can be, for example, a Doppler ultrasound system that is positioned on the chest wall and measures the aortic blood flow velocity. In the example depicted in FIG. 8, the delays are for a typical normal person. These delays will be different for patients suffering from CHF (congestive heart failure) or other cardiac malfunction (e.g., as depicted in FIG. 6).

FIG. 9 illustrates another embodiment of the present invention. The ASPPG 1 is responsive to control signals from the controller 7 to supply output signals to the first and second FGEs 2. The ASPPG 1 is connectable to the body external to, i.e., remote from, the heart, or at least the target heart tissue. The ASPPG 1 has a controllable output frequency, which changes in response to different control signals received from the controller 7. When the ASPPG 1 applies a pulse of AC to the FGEs 2, an electric field is created at a frequency that matches the pulse of AC. A plurality of rectifier-based receivers 3 are implanted at respective different positions within the target tissue (e.g., cardiac tissue in the left ventricle). Note that only one of those receivers 3 is depicted in FIG. 9—the other receivers 3 (not depicted) are similar to the depicted receiver 3, except that they are tuned to different frequencies. Each of the rectifier-based receivers 3 may be constructed using one or more rectifiers 30 combined with a filter 40. The filter 40 in each of the plurality of receivers 3 is set to a different frequency, so that for any given frequency, only one of the receivers 3 will generate an output pulse.

Other more complex filters can be used. Note also that active filters, etc. can also be utilized here by picking up the energy from the external current field, rather than using a battery. This stands in contrast to radio air-transmission, as the currents available there are negligible. Handshaking may additionally be employed for safety (anti hacking and electromagnetic interference) reasons. However, in this case more complex circuits are required. These may take the form of RFID systems without antennas or coils that are not necessary in this embodiment, as coupling is achieved through the conductive medium. Safety can also be augmented by surface electrodes or sensors, such as ECG 46, by means of which controller 7 can reject such issues. Additionally, the ECG can be used to synchronize the system with the natural cardiac activity, as many pacemakers do, or monitor the results of the rectifier-based receivers' stimulating electrical effects, for example, for use in modifying the relative timing and/or duration of the activation of the respective rectifier-based receivers.

Figure 10:
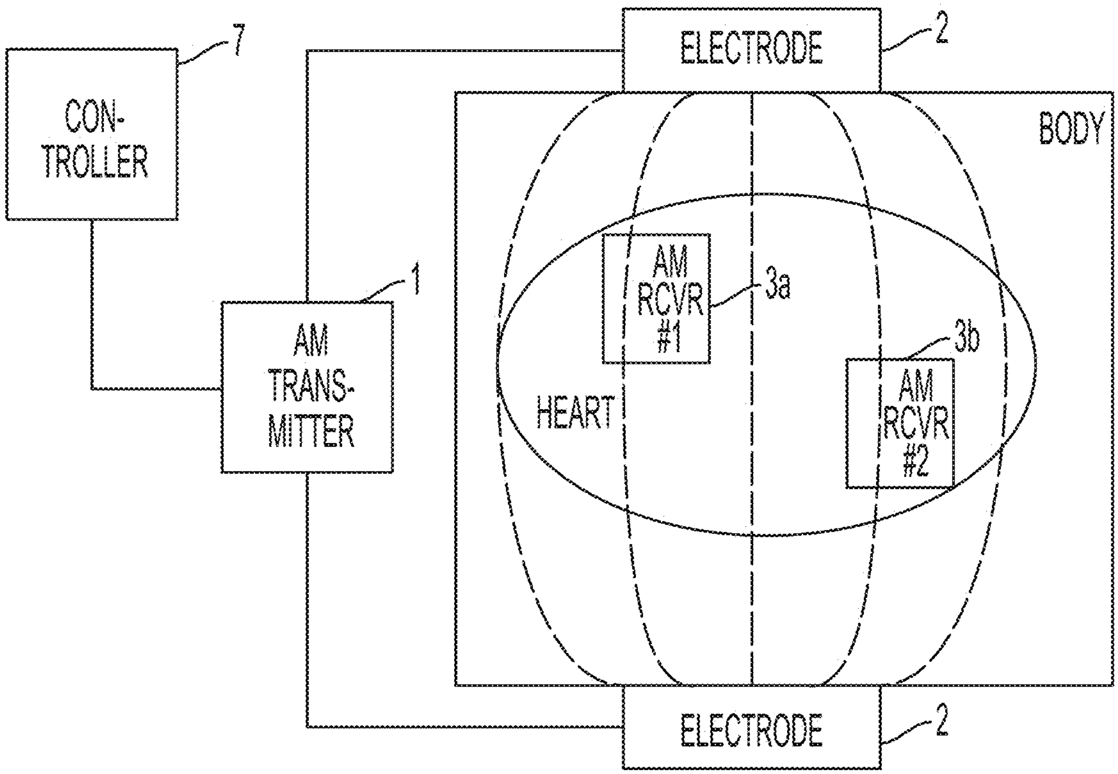
FIG. 10 is a block diagram of another embodiment of the present invention.

FIG. 10 is a block diagram of another embodiment of the present invention. As shown in FIG. 10, the AM transmitter 1 is responsive to control signals from the controller 7 to supply output signals to the first and second electrodes 2. The AM transmitter 1 is connectable to the body external to, i.e., remote from, the heart, or at least the target heart tissue. The AM transmitter 1 may be similar or identical to the ASPPG 1 in the embodiments described above; and the first and second electrodes 2 may be similar or identical to the FGE electrodes 2 in the embodiments described above. The AM transmitter 1 has a controllable output frequency in response to different control signals received from the controller 7. Thus, the AM transmitter 1 may output a first-frequency signal at a first frequency, e.g., 100 kHz, in response to a first control signal from the controller 7, and correspondingly the AM transmitter 1 may output a second-frequency signal at a second frequency, e.g., 200 kHz, in response to a second control signal from the controller 7. As indicated by the dashed lines in FIG. 10, the electrodes 2 create an electric field at the first or second frequency across the volume of the target heart tissue, which here is the left ventricle (LV). Implanted within the LV are first and second rectifier-based AM receivers 3*a*-3*b*, which are respectively labeled AM RCVR #1 (3*a*) and AM RCVR #2 (3*b*). The first AM receiver 3*a* has been implanted at a first position within the LV and the second AM receiver 3*b* has been implanted at a second position within the LV. Successive stimulation applied with appropriate timing and durations at the first and second positions is intended to promote normal cardiac activity. The construction of the rectifier-based AM receivers 3*a*, 3*b* may be as described above in connection with FIGS. 4-7.

To achieve this successive stimulation, each of the rectifier-based AM receivers 3*a*-3*b* is configured to be responsive to different frequencies of the applied electric field. This may be achieved within each AM receiver using a filter, e.g., a band pass filter, tuned to the appropriate frequency. The construction of these filters may be as described above in connection with FIG. 7D.

In the example of FIG. 10, the first AM receiver 3*a* may be tuned to a first frequency of 100 kHz, and therefore will receive and generate a first demodulated output signal capable of stimulating the LV only when the AM transmitter 1 generates the first-frequency output signal of 100 kHz. Correspondingly, the second AM receiver 3*b* may be tuned to a second frequency of 200 kHz, and therefore will receive and generate a second demodulated output signal capable of stimulating the LV only when the AM transmitter 1 generates the second-frequency output signal of 200 kHz. The first AM receiver 3*a* does not generate an output signal that is capable of stimulating the LV when the 200 kHz arrives at its antenna, and the second AM receiver 3*b* does not generate an output signal that is capable of stimulating the LV when the 100 kHz arrives at its antenna.

FIG. 11 is a timing diagram illustrating the respective activation times of the first and second AM receivers 3*a*-3*b* in accordance with timing and durations of the 100 kHz signal (the first-frequency output signal) and the 200 kHz signal (the second-frequency output signal), as discussed above in the exemplary operation of the embodiment of FIG. 10.

Note that while only two receivers 3*a*-3*b* are explicitly shown in FIG. 10, one or more additional AM receivers tuned to respective different frequencies may be implanted at respective different locations in the heart to provide a desired sequence of stimulation. For example, if one additional receiver 3 is implanted, there will be a total of three receivers, if two additional receivers 3 are implanted, there will be a total of four receivers, etc. Each such additional AM receiver 3 may operate in the same manner as the AM receivers 3*a*-3*b* discussed above, and the controller 7 can apply the appropriate control signal to the AM transmitter 1 to control generation of the respective frequency output signals.

When additional receivers are implanted, the controller 7 generates control signals that cause the AM transmitter to generate many different-frequency output signals at appropriate times during a cardiac cycle so that when the different-frequency output signals arrive at all the receivers, each receiver will generate a respective demodulated output signal that stimulates a respective part of the heart at a respective time within the cardiac cycle to promote improved cardiac performance. For example, if five receivers 3 are implanted at the five respective positions depicted in FIG. 8, the timing of the outputs issued by the controller 7 may be synchronized so that the outputs of all the implanted receivers will be activated at the respective times within the cardiac cycles depicted in FIG. 8.

In some preferred embodiments, the rectifier-based AM receivers 3 described above may be made completely from passive components such as diodes, capacitors, and inductors. These embodiments are particularly advantageous because there is no need to implant a power source into the subject's body to power these components. Instead, an electric field is imposed in the subject's body by hardware that is positioned outside the subject's body and powered from an external source. And the diodes rectify the imposed electric field to generate the relevant pacing pulses within the subject's body.

Experiments were performed to investigate the effect of half-wave rectified signals on rat hearts. These experiments used an AC signal generator that generated pulses of sinusoidal AC (relative to ground) at frequencies between 100 kHz and 1 MHz, with pulse durations between 0.5 and 10 ms. The output of the AC signal generator was connected to the anode of a rectifier, and the ground terminal of the AC signal generator was connected to a ground electrode positioned on the rat's shaved skin. Due to the action of the rectifier, the signal that exited the cathode of the rectifier was a pulse of half-rectified AC. The signal from the cathode of the rectifier was applied to the outer surface of the rat's right ventricle, via an electrode having a tip diameter of 1 mm. The pulses thus generated flowed from the AC signal generator output, through the rectifier, into the heart muscle and from it through various tissues to the ground electrode.

Figure 12:
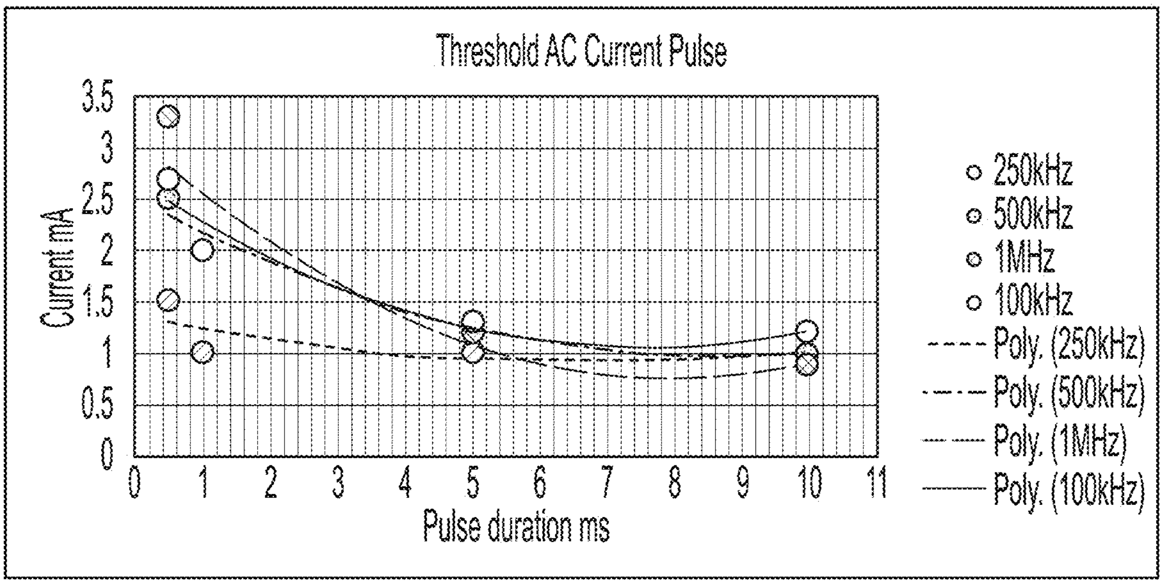
FIG. 12 depicts the results of experiments on rats that measured the threshold AC current intensity that provided cardiac stimulation.

FIG. 12 depicts the threshold current intensity that provided cardiac stimulation in these rat experiments for pulse durations of 0.5 ms, 1 ms, 5 ms and 10 ms using four different frequencies (100 kHz, 250 kHz, 500 kHz, and 1 MHz). The observed threshold current intensities are similar to those used in human cardiac pacing where mono or bipolar pulses in the range of ms are used.

Although the above discussion focusses on multisite resynchronization of the heart, the embodiments described above can advantageously be used for effective coordinated stimulation of other effects, where beneficial. More specifically, humans, and animals have numerous other complex excitable systems, for example, the brain, the vertebral (spinal) cord, limbs, and the torso muscle systems, etc. These systems consist of many elements, the function of which requires simultaneous or sequential excitation. In some cases, properly timed inhibitions are also required. Embodiments may also be advantageously used for multisite resynchronization of these systems.

Figure 13:
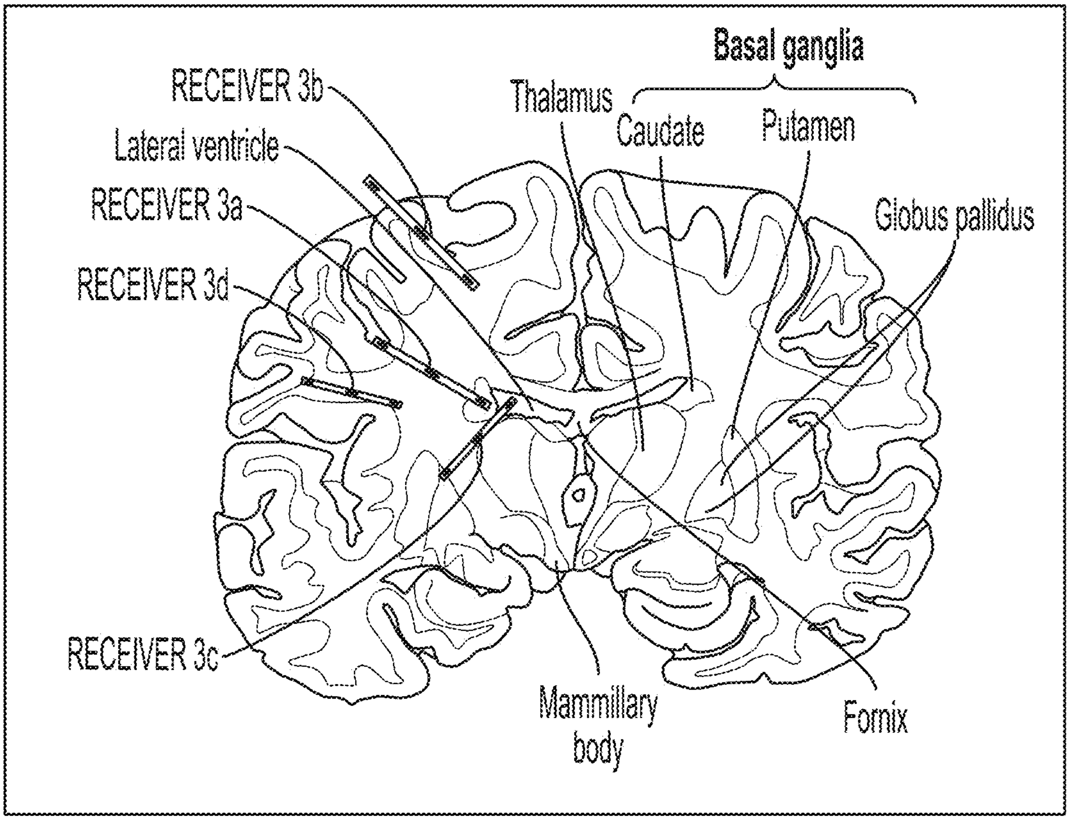
FIG. 13 is an illustration of the multisite positioning in the human brain of rectifier-based receivers in accordance with another embodiment of the present invention.

FIG. 13 depicts an example in the context of the brain where multi-site, timed excitation and/or inhibition can produce beneficial results regarding, for example, stopping tremor, seizures, developing neural pathologies, or initiating desired physiological or behavioral responses.

While the currents generated at the cathode of a rectifier in any given rectifier-based receiver usually cause excitation, the anode may induce inhibition. When a rectifier is employed to do either one of the above, the proper electrode is positioned at the site to be affected while the other electrode is preferably making contact with a "neutral site." Such a neutral site is generally an area in the heart, brain, etc. that, when affected, does not have a non-desired response, or is located outside the excitable tissue, for example, in the blood inside the heart chambers (see FIG. 3), in the space between the brain and meninges or skull, brain sulci or in the brain ventricles (see FIG. 13), etc.

The terminology used herein is for the purpose of describing particular embodiments and is not intended to be limiting. It will be understood that, although the terms first, second, third, etc. are used herein to describe various elements, components, frequencies, positions, etc., these elements, components, frequencies, positions, etc. should not be limited by these terms. These terms are used only to distinguish one element, component, frequency, position, etc. from another element, component, frequency, position, etc. Thus, a first element, component, frequency, position, etc. discussed herein could be termed a second element, component, frequency, position, etc. without departing from the teachings of the present application. Moreover, in reciting a number, e.g., first, second, and/or third, features or similar elements such as receivers, the claims are not to be interpreted as including only the recited number of such features, but may also include additional ones of such features or similar elements.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for stimulating a heart in a living body, the apparatus comprising:

an AM transmitter having a controllable output frequency, the AM transmitter being configured to generate a first-frequency output signal in response to a first control signal and to generate a second-frequency output signal in response to a second control signal, wherein the first frequency is at least 50 kHz, the second frequency is at least 50 kHz, and the first frequency is different from the second frequency;

a first AM receiver configured for implantation at a first position within the heart, wherein the first AM receiver includes a first antenna, at least one first rectifier, and a first filter that is tuned to the first frequency, wherein the first AM receiver is configured to (a) generate a first demodulated output signal that stimulates cardiac tissue concurrently with arrival of the first-frequency output signal at the first antenna and (b) not to generate an output signal that stimulates cardiac tissue in response to arrival of the second-frequency output signal at the first antenna;

a second AM receiver configured for implantation at a second position within the heart, wherein the second AM receiver includes a second antenna, at least one second rectifier, and a second filter that is tuned to the second frequency, wherein the second AM receiver is configured to (a) generate a second demodulated output signal that stimulates cardiac tissue concurrently with arrival of the second- frequency output signal at the second antenna and (b) not to generate an output signal that stimulates the cardiac tissue in response to arrival of the first-frequency output signal at the second antenna; and a controller configured to generate the first control signal and the second control signal and to control timing and duration of the generated first and second control signals so that the generated first and second control signals cause the AM transmitter to generate the first-frequency output signal and the second-frequency output signal at appropriate times during a cardiac cycle so that while the first-frequency output signal and the second-frequency output signal are being received by the first AM receiver and the second AM receiver, respectively, the first AM receiver and the second AM receiver generate the respective first and second demodulated output signals that stimulate respective parts of the heart to promote improved cardiac performance.

2. The apparatus of claim 1, wherein the controller is configured to control the timing of the generated first and second control signals such that there is a first delay between initiation of the first control signal and initiation of the second control signal, wherein the first delay is one of a predetermined delay, a selected delay based on a medical characteristic of the body, and a delay determined in accordance with a response of the cardiac tissue to at least one of the first and second demodulated output signals.

3. The apparatus of claim 1, wherein the AM transmitter is configured to be connectable to the body external to the heart.

4. The apparatus of claim 1, wherein each of the at least one first rectifier and the at least one second rectifier comprises four diodes arranged in a full-wave rectifier circuit.

5. The apparatus of claim 1, wherein each of the at least one first rectifier and the at least one second rectifier comprises a diode arranged in a half-wave rectifier circuit.

6. The apparatus of claim 1, wherein the first frequency is between 100 kHz and 1 MHz and the second frequency is between 100 kHz and 1 MHz.

7. The apparatus of claim 1, further comprising:

a third AM receiver configured for implantation at a third position within the heart, wherein the third AM receiver includes a third antenna, at least one third rectifier, and a third filter, wherein the AM transmitter is further configured to generate a third-frequency output signal in response to a third control signal, wherein the third frequency is at least 50 kHz, and wherein the third frequency is different from the first frequency and also different from the second frequency, wherein the third filter is tuned to the third frequency, and the third AM receiver is configured to (a) generate a third demodulated output signal that stimulates cardiac tissue concurrently with arrival of the third-frequency output signal at the third antenna and (b) not to generate an output signal that stimulates cardiac tissue in response to arrival of the first-frequency output signal at the third antenna or in response to arrival of the second-frequency output signal at the third antenna, wherein the controller is further configured to generate the third control signal and to control timing and duration of the generated first, second, and third control signals so that the generated first, second, and third control signals cause the AM transmitter to generate the first-frequency output signal, the second-frequency output signal, and the third-frequency output signal at appropriate times during a cardiac cycle so that while the first-frequency output signal, the second-frequency output signal, and the third-frequency output signal are being received by the first, second, and third AM receivers, respectively, the first, second, and third AM receivers generate the respective first second, and third demodulated output signals that stimulate respective parts of the heart to promote improved cardiac performance, and wherein the first AM receiver is configured not to generate an output signal that stimulates cardiac tissue in response to arrival of the third-frequency output signal at the first antenna, and the second AM receiver is configured not to generate an output signal that stimulates cardiac tissue in response to arrival of the third-frequency output signal at the second antenna.

8. The apparatus of claim 7, wherein the controller is configured to control the timing of the generated first, second, and third control signals such that there is a second delay between initiation of the second control signal and initiation of the third control signal, wherein each of the first and second delays is one of a predetermined delay, a selected delay based on a medical characteristic of the body, and a delay determined in accordance with a response of the cardiac tissue to at least one of the first, second, and third demodulated output signals.

9. The apparatus of claim 7, wherein the third frequency is between 100 kHz and 1 MHz.

10. A method for stimulating a heart in a living body, the method comprising the steps of:

transmitting an AM signal at a first frequency at certain first times and an AM signal at a second frequency at certain second times, wherein the first frequency is at least 50 kHz, the second frequency is at least 50 kHz, and the first frequency is different from the second frequency;

receiving the AM signal at the first frequency at a first position within the heart;

generating a corresponding first demodulated output signal that stimulates cardiac tissue concurrently with arrival of the AM signal at the first frequency, wherein an output signal that stimulates cardiac tissue is not generated in response to arrival of the AM signal at the second frequency at the first position;

receiving the AM signal at the second frequency at a second position within the heart;

generating a corresponding second demodulated output signal that is capable of stimulates cardiac tissue concurrently with arrival of the AM signal at the second frequency, wherein an output signal that stimulates cardiac tissue is not generated in response to arrival of the AM signal at the first frequency at the second position; and controlling generation, timing, and duration of the AM signal at the first frequency and the AM signal at the second frequency at appropriate times during a cardiac cycle so that while the AM signal at the first frequency and the AM signal at the second frequency are being received at the first and second positions, respectively, the generated first and second demodulated output signals stimulate respective parts of the heart to promote improved cardiac performance.

11. The method of claim 10, further comprising the step of controlling the timing of the AM signal at the first frequency and the AM signal at the second frequency such that there is a first delay between initiation of the first AM signal at the first frequency and initiation of the second AM signal at the second frequency, wherein the first delay is one of a predetermined delay, a selected delay based on a medical characteristic of the body, and a delay determined in accordance with a response of the cardiac tissue to at least one of the first and second demodulated output signals.

12. The method of claim 10, wherein the transmitting of the AM signal occurs through the body from a position of the body external to the heart.

13. The method of claim 10, wherein the first frequency is between 100 kHz and 1 MHz and the second frequency is between 100 kHz and 1 MHz.

14. The method of claim 10, further comprising the steps of:

transmitting the AM signal at a third frequency at certain third times, wherein the third frequency is at least 50 kHz, and wherein the third frequency is different from the first frequency and also different from the second frequency; and receiving the AM signal at the third frequency at a third position within the heart;

generating a third demodulated output signal that stimulates cardiac tissue concurrently with arrival of the AM signal at the third frequency, wherein an output signal that stimulates cardiac tissue is not generated in response to arrival of either the AM signal at the first frequency or the AM signal at the second frequency at the third position, wherein the controlling step includes the steps of controlling generation of the AM signal at the third frequency and controlling timing and duration of the AM signals at the first, second, and third frequencies at appropriate times during a cardiac cycle so that while the AM signals at the first, second, and third frequencies are being received at the first, second, and third positions, respectively, the generated first second, and third demodulated output signals stimulate respective parts of the heart to promote improved cardiac performance, and wherein no output signal capable of stimulating cardiac tissue is generated in response to arrival of the AM signal at the third frequency at either the first position or the second position.

15. The method of claim 14, wherein the controlling step controls the timing of the AM signals at the first, second, and third frequencies such that there is a second delay between initiation of the AM signal at the second frequency and initiation of the AM signal at the third frequency, wherein each of the first and second delays is one of a predetermined delay, a selected delay based on a medical characteristic of the body, and a delay determined in accordance with a response of the cardiac tissue to at least one of the first, second, and third demodulated output signals.

16. The method of claim 15, wherein the third frequency is between 100 kHz and 1 MHz.

17. An apparatus for stimulating designated animal tissue in a living body, the apparatus comprising:

an AM transmitter having a controllable output frequency, the AM transmitter being configured to generate a first-frequency output signal in response to a first control signal and a second-frequency output signal in response to a second control signal, wherein the first frequency is at least 50 kHz, the second frequency is at least 50 kHz, and the first frequency is different from the second frequency;

a first AM receiver configured for implantation at a first position within the tissue, wherein the first AM receiver includes a first antenna, at least one first rectifier, and a first filter that is tuned to the first frequency, wherein the first AM receiver is configured to (a) generate a first demodulated output signal that stimulates the tissue concurrently with arrival of the first-frequency output signal at the first antenna and (b) not to generate an output signal that stimulates the tissue in response to arrival of the second-frequency output signal at the first antenna;

a second AM receiver configured for implantation at a second position within the tissue, wherein the second AM receiver includes a second antenna, at least one second rectifier, and a second filter that is tuned to the second frequency, wherein the second AM receiver is configured to (a) generate a second demodulated output signal that stimulates the tissue concurrently with arrival of the second-frequency output signal at the second antenna and (b) not to generate an output signal that stimulates the tissue in response to arrival of the first-frequency output signal at the second antenna; and a controller configured to generate the first control signal and the second control signal and to control timing and duration of the generated first and second control signals so that the generated first and second control signals cause the AM transmitter to generate the first-frequency output signal and the second-frequency output signal at appropriate times during an activity of the tissue so that while the first-frequency output signal and the second-frequency output signal are being received by the first AM receiver and the second AM receiver, respectively, the first AM receiver and the second AM receiver generate the respective first and second demodulated output signals that stimulate the tissue.

18. The apparatus of claim 17, wherein the controller is configured to control the timing of the generated first and second control signals such that there is a first delay between initiation of the first control signal and initiation of the second control signal, wherein the first delay is one of a predetermined delay, a selected delay based on a medical characteristic of the tissue, and a delay determined in accordance with a response of the tissue to at least one of the first and second demodulated output signals.

19. The apparatus of claim 17, wherein the AM transmitter is configured to be connectable to the body external to the tissue.

20. The apparatus of claim 17, wherein the first frequency is between 100 kHz and 1 MHz and the second frequency is between 100 kHz and 1 MHz.

* * * * *